(12) United States Patent
Casset

(10) Patent No.: US 8,798,748 B2
(45) Date of Patent: Aug. 5, 2014

(54) PREDICTIVE DIAGNOSIS OF A PATIENT'S STATUS IN AN ACTIVE IMPLANTABLE MEDICAL DEVICE NOTABLY FOR CARDIAC PACING, RESYNCHRONIZATION, DEFIBRILLATION OR CARDIOVERSION

(75) Inventor: Cyrille Casset, Paris (FR)

(73) Assignee: Sorin CRM S.A.S., Clamart Cedex (FR)

( * ) Notice: Subject to any disclaimer, the term of this patent is extended or adjusted under 35 U.S.C. 154(b) by 1504 days.

(21) Appl. No.: 11/535,942

(22) Filed: Sep. 27, 2006

(65) Prior Publication Data

US 2007/0073350 A1 Mar. 29, 2007

(30) Foreign Application Priority Data

Sep. 27, 2005 (FR) ...................................... 05 09837

(51) Int. Cl.
*A61N 1/362* (2006.01)
(52) U.S. Cl.
USPC .................................. 607/18; 607/17; 607/19
(58) Field of Classification Search
USPC .......... 607/19, 17–18; 128/897, 923; 600/300
See application file for complete search history.

(56) References Cited

U.S. PATENT DOCUMENTS

| 4,417,592 | A | * | 11/1983 | John ................................ 600/544 |
| 5,722,996 | A | * | 3/1998 | Bonnet et al. .................... 607/17 |
| 6,128,534 | A | * | 10/2000 | Park et al. ........................ 607/17 |
| 6,246,910 | B1 | | 6/2001 | Bonnet et al. |
| 6,336,048 | B1 | | 1/2002 | Bonnet |
| 6,731,984 | B2 | * | 5/2004 | Cho et al. ........................ 607/17 |
| 6,741,885 | B1 | * | 5/2004 | Bornzin et al. ................ 600/509 |
| 7,010,347 | B2 | * | 3/2006 | Schecter .......................... 607/17 |
| 7,206,635 | B2 | * | 4/2007 | Cho et al. ........................ 607/17 |
| 2001/0037067 | A1 | | 11/2001 | Tchou et al. |
| 2004/0039420 | A1 | * | 2/2004 | Jayne et al. ........................ 607/5 |
| 2005/0080460 | A1 | * | 4/2005 | Wang et al. ..................... 607/17 |
| 2005/0256545 | A1 | * | 11/2005 | Koh et al. ........................ 607/17 |
| 2007/0021678 | A1 | * | 1/2007 | Beck et al. ..................... 600/510 |
| 2007/0179390 | A1 | * | 8/2007 | Schecter ....................... 600/508 |

FOREIGN PATENT DOCUMENTS

| EP | 0750920 | 2/1997 |
| EP | 0804939 | 5/1997 |
| EP | 0919255 | 6/1998 |
| EP | 0966987 | 12/1999 |
| EP | 1317943 | 11/2003 |

* cited by examiner

*Primary Examiner* — Carl H Layno
*Assistant Examiner* — Jennifer Ghand
(74) *Attorney, Agent, or Firm* — Foley & Lardner LLP

(57) ABSTRACT

An active implantable medical device or pacing, resynchronization defibrillation and/or cardioversion, and/or a device for diagnosing patient conditions, having a predictive diagnosis of the patient's status. The device measures a physiologic parameter, notably the minute ventilation; measures a physical parameter, notably the acceleration; discriminates between phases of activity and rest of the patient; and includes a memory containing a plurality of fields selectively updated by statistical processing. These fields are comprising one first set containing data related to the patient's activity phases, and one second set containing data related to the patient's rest phases. The statistical processing is updating in a dissociated manner the first and second sets of fields, selectively as a function of the value taken by the status indicator, and the analysis evaluates at least one clinical status index based upon the data contained in the fields of both first and second sets.

18 Claims, 3 Drawing Sheets

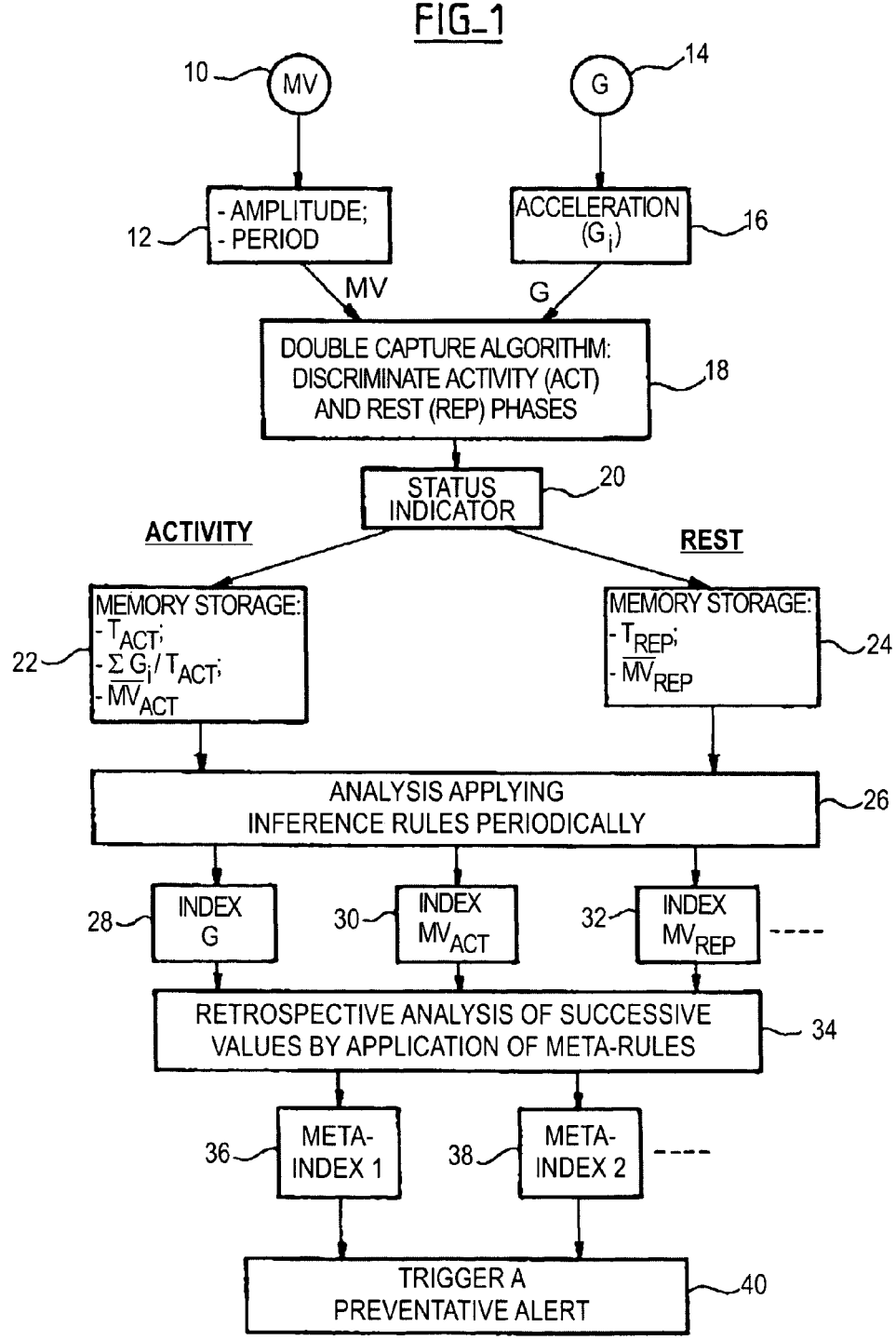

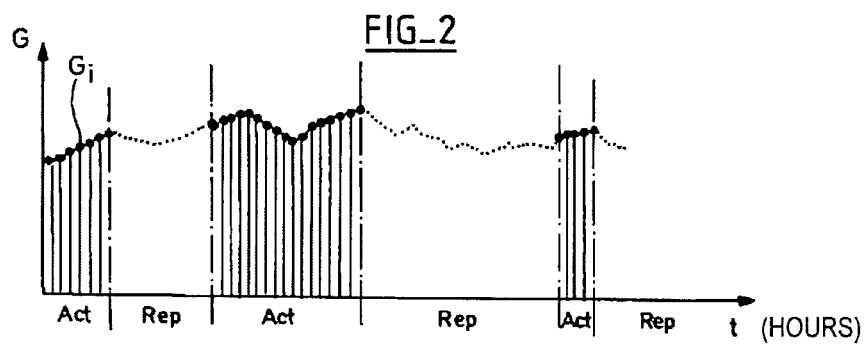
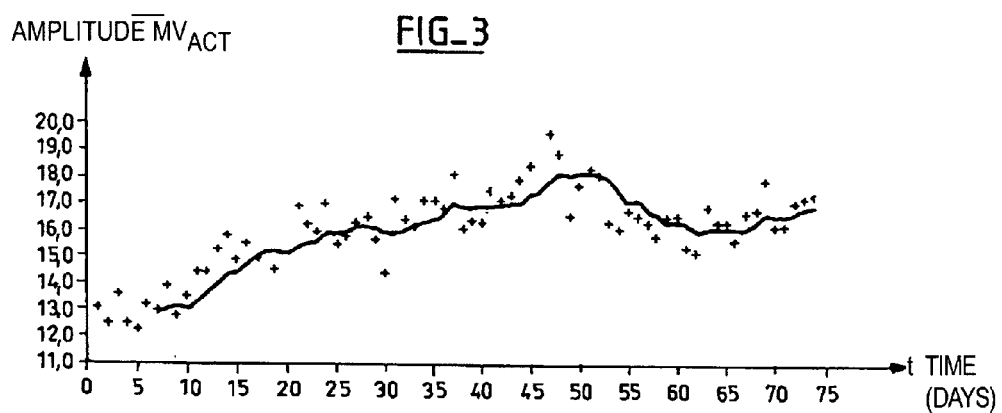
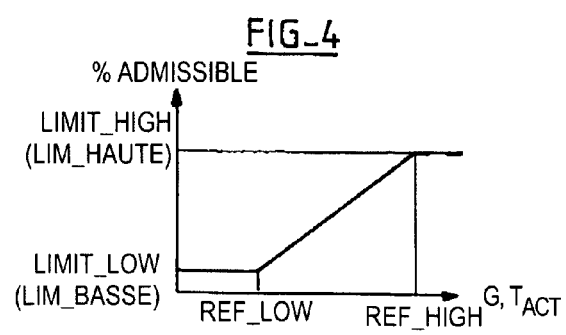

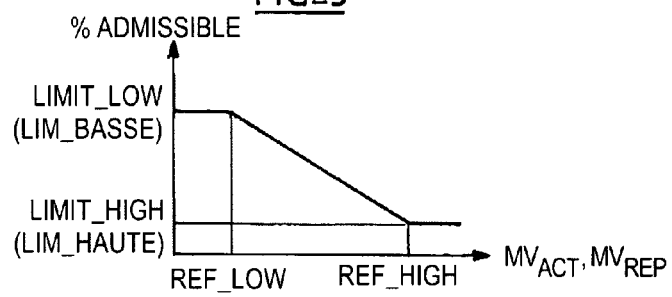
FIG_5
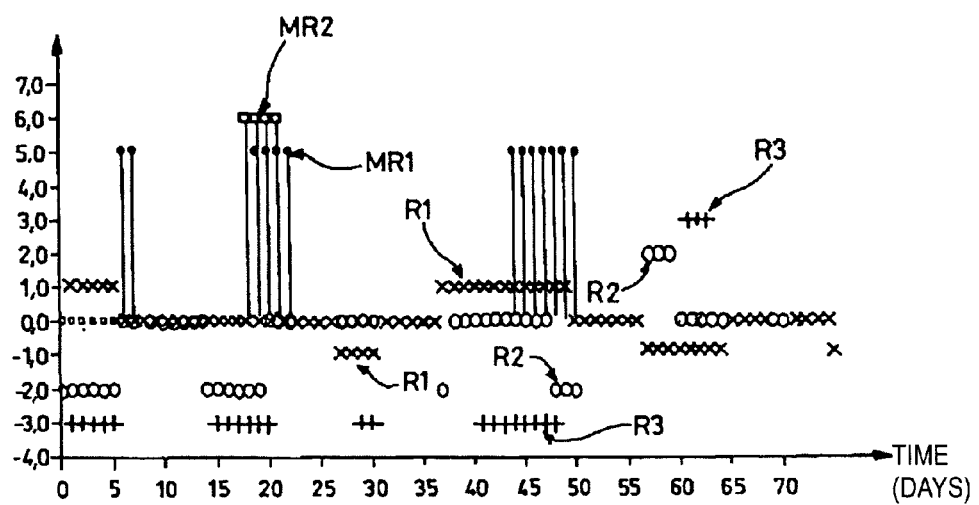
FIG_6

PREDICTIVE DIAGNOSIS OF A PATIENT'S STATUS IN AN ACTIVE IMPLANTABLE MEDICAL DEVICE NOTABLY FOR CARDIAC PACING, RESYNCHRONIZATION, DEFIBRILLATION OR CARDIOVERSION

FIELD OF THE INVENTION

The present invention relates to "active implantable medical devices" as such devices are defined by the Jun. 20, 1990 Directive 90/385/CEE of the Counsel of the European Community, and more particularly to cardiac pacemakers, cardiac resynchronization devices, cardioverters and/or defibrillators intended for the treatment of cardiac rhythm disorders, and/or active implantable devices intended for diagnosis of cardiac rhythm. It is more particularly related to such devices whose operation is responsive to parameters collected by sensors allowing to assess metabolic needs of the patient, as well as the patient's current level of activity.

BACKGROUND OF THE INVENTION

Implantable medical devices that respond to a patient's metabolic needs are known that include two different kinds of sensors, i.e. one sensor for the measurement of a corporal parameter that is predominantly physiologic, and one sensor for the measurement of a corporal parameter that is predominantly physical.

One will hereinafter refer to the particular example of a minute-ventilation (also sometimes known as "minute volume") (MV) sensor as the physiologic sensor, corresponding to the most usual case, but it should be understood that this example is in no way limiting, and that other types of sensors also may be used, so long as they provide a signal that is representative of the patient's metabolic needs (for example, a sensor that is measuring blood oxygen saturation) or his hemodynamic status (for example, an intracardiac bioimpedance sensor) based on a physiological parameter. Likewise, one will hereinafter refer to the particular example of an acceleration (G) sensor as the physical (or activity) sensor, corresponding to the most usual case, but here, too, it should be understood that some other type of sensor can be considered, notably to detect the patient's movements.

Generally, the physical (activity) sensor is characterized by a response time that is shorter than that of the physiological sensor, in order to allow a very fast detection of short-duration activity, before a significant change of the physiological parameter, which varies more slowly, is detected.

The European patent EP 0750920, and its counterpart U.S. Pat. No. 5,722,996, commonly assigned herewith to ELA Medical, are proposing such a device that is enslaved, i.e. responsive to, two such sensors, operating a selection of one or the other sensor so as to take into account only the sensor that gives the more relevant signal at any given moment. The European patent EP 0919255 and its counterpart U.S. Pat. No. 6,336,048, commonly assigned herewith to ELA Medical, are proposing an enslavement based upon the use of a combination of the signals provided by these two sensors.

Besides enslavement, the signals provided by the sensors may be used for the purpose of diagnosing heart failure, so as to properly adjust the operation of the implanted device. Particularly, the European patent EP 0966987 and its U.S. counterpart U.S. Pat. No. 6,246,910, commonly assigned herewith to ELA Medical, allow to follow up evolution of the patient's condition over time so as to give an adequate representation of the patient's actual metabolic requirements, i.e. taking into account the actual activity level of the patient. The device described in that document adjusts its operation in case of a detected worsening or improvement of the patient's status, for example by reprogramming some of its functions, in order to follow the patient's evolution and adapt to the patient's effective cardiac decompensation level.

The starting point of the present invention lies in the inventor's observation of patients who, though actually implanted with improved devices, are adapting their own daily activity to the changes in their clinical status, with an incidence on their activity level, and, in some cases, on their respiratory status. Indeed, as it has been discovered, the clinical modifications are likely to be asymptomatic, and it is usual that the patient unconsciously adapts his activity to his clinical status: the first crisis of heart failure appearing during activity, the patient is led to reduce his activity in order to avoid the occurrence of such crisis. Hence, the symptoms no longer occur, the patient having changed his behavior so as to prevent them, but the pathology nevertheless keeps on evolving. Thus, the patient will go and visit his physician again, no sooner than when his heart failure will disturb him even when he is at rest, and in a worst case, the patient will have to turn to the emergency room for treatment.

In summary, due to such auto-adaptation, the absence of symptoms perceived by the patient leads to a significant delay between the onset of clinical modifications and the actual diagnosis thereof, the latter likely being too late.

OBJECTS AND SUMMARY OF THE INVENTION

It is therefore an object of the present invention to propose a device of the type referred to above, that is: an implantable device equipped with two sensors, one predominantly physiologic, and one predominantly physical (activity), that is able to process the information provided by these two sensors, so as to assess the actual status of the patient and the evolution of his pathology, even in the absence of any felt symptoms, and even if the patient is unconsciously adapting his behavior to the evolution of his clinical status (i.e., even if he is reducing his physical activity to prevent an occurrence of heart failure crisis).

It is a further object of this invention to propose a device to aid the diagnosis that, based upon clinical status data thus evaluated, allows to anticipate a worsening of heart failure by subsequently adapting the patient's treatment, or by modifying the device's operation.

It is yet another object of the invention to propose such a device that allows to detect a sudden worsening of the patient's clinical status, even in the absence of any serious symptoms, and to trigger a preventive alarm signal that allows to take, as soon as possible, appropriate measures thus avoiding the sudden triggering of a short-term crisis.

The patient's clinical status is reflected in the form of one or more clinical status indices, for example, which is completed and updated by the device on a periodic, preferably daily, basis.

As for a predictive diagnosis, it is based upon the evolution of the one or more clinical status indices over a long term point of view, through analyzing variations over a period of, for example, many days. Such an analysis can be made on a daily basis, by the device itself (i.e., internally) or by means of an external device (i.e., a programmer), for instance in order to display the different indices, and present the results on a screen for evaluation by a practitioner.

One aspect of the present invention is broadly directed to a device of the dual sensor type, as the devices described in the documents referred to above, that is: comprising: means for measuring a corporal parameter that is predominantly physiologic, preferably minute ventilation, and providing a physiologic signal; means for measuring a corporal parameter predominantly physical, preferably acceleration, and providing a physical signal; means for discrimination between rest and activity phases of the patient, operating in response to said physiologic and physical signals, and providing an indication of the patient's status; a memory containing a plurality of fields; and means for statistical processing, able to receive, as input data, physiologic signals, physical signals and status indicator, and deliver as output data, processed information and to selectively update said memory fields based upon said processed information.

In a characteristic manner of the invention, said memory fields preferably comprise a first set of fields containing data related to the patient's activity phases, and a second set of fields containing data related to the patient's rest phases. The means for statistical processing operate to update the first and second sets of fields in a dissociated manner, selectively as a function of the value of the status indicator, and the device further comprises means for analysis, able to evaluate at least one clinical status index based upon the data contained in the memory fields of both the first and second sets.

The first set of fields may preferably comprise fields that are representative of the elapsed duration of activity, and the second set of fields that are representative of the elapsed duration of rest and the level of physiologic signal over that elapsed duration of rest.

The field representative of the level of the physical signal can particularly be a field containing a rollup (an accumulation) of successive digitized values of the physical signal over a predetermined duration, that rollup being operated only when the status indicator shows an exercise activity.

The fields representative of the level of the physiologic signal can be fields containing an average of successive digitized values of the physiologic signal over a predetermined duration, that average being updated only when the status indicator shows a phase, respectively of activity or rest.

The means for analysis may comprise means for comparing at least some of said data, or variations thereof, to a reference value. The latter is advantageously a calculated value, that is a function of the average level of corresponding data over a predetermined duration, and may be bounded by upper and lower bounds.

Advantageously, the means for analysis are also able to evaluate at least one meta-index based upon successive values of the clinical status index, notably in order to implement means for determining a preventive alert, able to warn of the overshoot (i.e., crossing) of a threshold by at least one of these meta-indices. The indices and meta-indices are periodically re-evaluated preferably daily.

BRIEF DESCRIPTION OF THE DRAWINGS

Further features, advantages and characteristics of the present invention will become apparent to a person of ordinary skill in the art in view of the following detailed description of preferred embodiments of the invention, made with reference to the drawings annexed in which like reference characters refer to like elements, and in which:

FIG. 1 is a block diagram showing a determination of a clinical status index and a predictive diagnosis of a device in accordance with a preferred embodiment of the invention;

FIG. 2 shows a graph of variations of an acceleration signal over time as are taken into account by the device of FIG. 1;

FIG. 3 shows variations of a mean minute ventilation signal over time when in activity, over a duration of a few weeks;

FIG. 4 shows a transfer function for the determination of the clinical status index related to the acceleration and elapsed duration in activity phase in the process of FIG. 1;

FIG. 5 shows the transfer function for the determination of the clinical status index related to minute ventilation during activity and at rest in the process of FIG. 1; and FIG. 6 is one example of a display of the different clinical status indices and diagnosis meta-indices determined by the device of FIG. 1.

DETAILED DESCRIPTION OF THE INVENTION

With reference to FIGS. 1-6; one will now describe a preferred embodiment of a device in accordance with the present invention. Regarding the software-related aspects thereof, the functionality and processes of the present invention can be implemented by an appropriate programming of the software of a known enslaved (rate-responsive) pacemaker. The invention can preferably be applied to the commercial implantable devices marketed by ELA Medical, Montrouge, France, such as the Symphony and Rhapsody brand pacemakers and comparable commercial and/or proprietary devices of other manufacturers. These devices are equipped with programmable microprocessors, including circuits intended to acquire, format and process electrical signals collected by implanted electrodes and various sensors. It is also possible to upload towards these devices, by telemetry, pieces of software that will be stored in internal memory and run so as to implement the features and functionality of the invention, described in more detail below. Implementing the features of the invention into these devices is believed to be easily feasible by a person of ordinary skill in the art, and will therefore not be described in detail in this document.

As shown in FIG. 1, the device comprises a sensor 10 providing a signal that is representative of the patient's metabolic demand, typically a transthoracic impedance signal, the analysis of periodical variations thereof (amplitudes and successive periods) being performed by block 12 that provides a minute ventilation (MV) signal. The device also comprises a physical sensor allowing to sense the patient's movements, typically an acceleration (G) sensor 14 associated with a sampling circuit 16 providing a succession of digitized samples $G_i$ with a step i=125 ms for instance.

Based upon concurrently provided MV and G information, the device performs an enslavement of the "dual sensor" type (block 18) as described in the aforementioned EP A 0750920 and EP A 0919255 and their US counterpart U.S. Pat. Nos. 9,722,991 and 6,336,048, which disclosures are hereby incorporated herein by reference in their entirety, preferably a control of pacing rate and eventual adaptation of operating parameters. That enslavement function is not per se part of this invention, yet is discussed in the incorporated references and so will not be described in detail in this document.

However, the enslavement algorithm has the advantage of comprising a discrimination function, between phases of activity and phases of rest of the patient (block 18), based upon instantaneous indications from MV and G sensors, resulting in a status indicator 20 able to take at least two values of "activity" and "rest" (some other values being possible, for example, "recovery after exercise", that will be assumed to be an activity phase, or "sleep" which is a particular case of rest phase).

This invention proposes to store the data provided by MV and G sensors into the device memory, in distinct ways for activity phases and rest phases. More precisely, the device comprises a first memory 22 gathering the characteristic parameters in activity phase, notably:

the time elapsed in activity phase over the last 24 hours ($T_{act}$), the sum of the measurements of G sensor in activity phase, weighted over the last 24 hours ($\Sigma G_i/T_{act}$), and the mean minute ventilation ($MV_{act}$) over the activity phases, measured over the last 24 hours.

FIG. 2 shows more precisely the manner that the data $\Sigma G_i$ is being obtained and updated. As stated above, the G sensor provides a series of digitized samples $G_i$ with step intervals of i=125 ms for example, of which the variations over time is shown in FIG. 2.

Also, the status indicator 20 allows to distinguish between activity phases (Act) and rest phases (Rep). The device proceeds to the summing of the values $G_i$ of the samples over the last 24 hours, but inhibits that summing during rest phases, thus only summing values corresponding to periods of activity. A weighted value is obtained by dividing the total of that summing (over the last 24 hours) by the duration of the activity phase $T_{act}$.

FIG. 3 shows an example of the variations of this parameter $MV_{act}$ over time for a duration of several weeks: the crosses indicate values that are computed everyday, and stored into the memory 22, the full line representing a moving average over 7 days.

The device further comprises a second memory 24 gathering the characteristic parameters in rest phase, notably:
the time elapsed at rest over the last 24 hours ($T_{rep}$), and
the average minute ventilation ($MV_{rep}$) during rest phases, measured over the last 24 hours.

The parameter $MV_{rep}$ is an average of minute ventilation MV during rest periods.

These various information, memorized and updated in the two arrays of values 22 and 24 are then subjected to an analysis (block 26) applying a certain number of inference rules providing a series of clinical indices, such as an index 28 related to the acceleration (index G), an index 30 related to minute ventilation in activity (index $MV_{act}$), an index 32 related to minute ventilation at rest ($MV_{rep}$), etc.

That analysis is performed periodically, for example, each day, with a daily update of the various clinical status indices.

Some different methods of analysis are possible. A first method involves comparing the stored values with various fixed references, and detecting the overshoot of low and/or high thresholds.

One other advantageous method that will be described in detail below concerns analyzing the variations of data from one day to the following day (or over any other periodic interval, such as from one week to the following week, etc.) and comparing that variation to a reference value corresponding to a physiologically admissible variation, taking into account the clinical status of the patient. The overshoot of that limit will reveal the degradation of the patient's status in view of the corresponding criterion (activity, basal ventilation, etc.).

One will now describe in detail for example the inference rule corresponding to the criterion G, the rules corresponding to the other criteria being applied similarly.

The memory 22 containing the parameters related to activity phases contains a series of values Somme_G(i), the step i corresponding here to a time interval of one day.

Rather than applying the inference rule to the isolated daily value, one preliminarily calculates a moving average over one week, so as to weight the variations of activity from one day to the next, that average can be expressed by following formula:

$$M7G(i) = (1/7) * \sum_{k=i-6}^{i} \text{somme\_G}(k)$$

The rule related to the parameter G will be referred to as "rule R1", and the result of its application will be an indicator likely to endorse three values, representative of the evolution of the patient's clinical status in view of that parameter G: +1 (improvement), −1 (degradation) and 0 (stability).

Indeed, the increase of activity is a favorable element in the patient's clinical array, which justifies the score +1, while a reduction of the patient's activity is conversely a unfavorable on a long term viewpoint.

These values are determined by the following formulae:
Rule R1:

If $M7G(i) > M7G(i-6)*\alpha(M7G(i))$, then $R1(i)=+1$;

If $M7G(i) < M7G(i-6)*\alpha(M7G(i))$, then $R1(i)=-1$;

Else $R1(i)=0$ $\alpha(M7G(i))$ being a percentage calculated based upon a transfer function that is depending upon the current value of the considered criterion.

The purpose of the a factor that is not constant is related to the need for taking into account the previous results, in order to qualify the improvement or degradation of the result: hence, for a patient with a very low activity, an increase of activity, even modest, will be a very favorable element, which is not necessarily the case for a patient with a sustained activity and a regular increase.

FIG. 4 shows the transfer function providing the admissible increase rate (hereafter referred to as ParameterThreshold) as a function of the value of considered parameter.

In the above referred-to example of parameter G, the transfer function is defined by the following formulae:

ParameterThreshold($M7(i)$)=Lower_Limit if $M7(i)$<Low_Ref

ParameterThreshold($M7(i)$)=Higher_Limit if $M7(i)$>High_Ref;

ParameterThreshold($M7(i)$)=$A*M7(i)+B$,

A, B being the slope and intercept point of the straight line defined by the points (Low_Ref, Lower_Limit) and (High_Ref, Higher_Limit).

The principle of that transfer function is also applicable, mutatis mutandis, to the elapsed duration in activity $T_{act}$.

However, as for the ventilation parameter, in activity ($MV_{act}$) or at rest ($MV_{rep}$), the direction of the variation of the transfer function shall be reversed, as shown on FIG. 5. Indeed, in the case when a patient has a high rest minute ventilation, even a very low increase may strongly impede him, though a patient with a lower ventilation still has a high margin of increase.

The results thus obtained through the application of various rules may be subjected to a more thorough diagnosis, through the application of meta-rules allowing to define one or more higher-level indices, or "meta-indices".

Those meta-indices are determined (block 34) through retrospective analysis of the successive values taken by the different indices.

Those meta-rules may be built up through several ways, and only one example thereof will be provided in the following, namely defining a limit over several days (p days) over which a rule R has to provide a minimum number of positive values for the corresponding index (that minimum being parameterized to the MR_Threshold value):

Meta-rule MR (one value +1 of the meta-index being representative of a significant aggravation of the patient's status):

$$MR(i) = \sum_{k=i-p+1}^{i} R(k), \text{ with } p \text{ being a natural number}$$

If $MR(i) > MR\_Threshold$, then $MR(i) = +1$; Else $MR(i) = 0$

That meta-rule takes into account the fact of having null or negative index values: indeed, null values do not increase the value MR(i) of the meta-index, whereas negative values have the effect of "compensating" the positive values lately taken.

Thus one or many meta-indices are obtained: 36, 38, ... reflecting the evolution of one of the parameters G, $MV_{act}$, $MV_{rep}$, ... or a combination of these various parameters.

Everything can be viewed or displayed, for example, in order to allow a practitioner to quickly seize the evolution of the patient's clinical status and assess the risks of sudden aggravation of that status.

A representative example of such a display is proposed on FIG. 6.

Each unit of abscissa corresponds to one day, and the determined values for the following are displayed for each day: the index related to the activity G (resulting from the application of the rule R1 and represented by a "X"), the index related to ventilation during activity $MV_{act}$ (resulting from the application of the rule R2 represented by an "O"), and the index related to the ventilation at rest $MV_{rep}$ (resulting from the application of the rule R3 and represented by a "+").

For the sake of display clarity, and in order to prevent any risk of overlay, the marker corresponding to the value ±1 of rule R1 was placed at the abscissa ±1, the marker corresponding to the value ±1 of rule R2 at the abscissa ±2 and the marker corresponding to the value ±1 of rule R3 at the abscissa ±3.

It can be seen on the illustrated example, that the rule R2 related to the ventilation in activity, shows an aggravation of the patient's status (increase of the ventilation in activity) on the dates 14 ... 19, 37, and 48 ... 50, an improvement of the patient's status (lowering of ventilation in activity) on the dates 57 ... 59, and a stationary status elsewhere. These results shall be compared with those illustrated on FIG. 3, that present a variation of the parameter $MV_{act}$ day after day.

The display also provides the results of the meta-rules, with the meta-indices MR1 and MR2: the marker corresponding to the value +1 of meta-rule R1 was placed at abscissa +4, the marker corresponding to the value +1 of meta-rule R2 was placed at abscissa +5. The meta-index MR1 results for example from the application of a meta-rule to rest ventilation, while the meta-index MR2 results from the application of a meta-rule combining the activity level with the activity ventilation.

Thus, on dates 44 ... 50, the meta-index MR1 signals an aggravation of the patient's status related to rest ventilation, provided the index R3 took the value −1 over at least 5 days out of 7.

Some alarms may be triggered as a function of the results given by the meta-rules (and also by the rules).

These alarms allow to anticipate the occurrence of an event such as heart failure, so as to take necessary measures with no delay in order to prevent the occurrence of this crisis or, at least to reduce its effects. That diagnosis can thus be done very early, before any serious symptom appears and therefore well before the patient has called his practitioner or visited an emergency room department.

One skilled in the art will appreciate that the present invention may be practiced by other than the foregoing embodiments, which are presented for purposes of illustration and not of limitation.

I claim:

1. An active implantable medical device for pacing, resynchronization, defibrillation, cardioversion and/or, diagnosis, comprising:
    means for measuring a predominantly physiologic corporeal parameter of a patient and providing a physiologic signal;
    means for measuring a predominantly physical corporeal parameter of the patient and providing a physical signal;
    means for discriminating between activity phases and rest phases of the patient, operating in response to said physiologic and physical signals, and providing a status indicator representative of the patient's status,
    a memory containing a plurality of fields, said plurality of fields comprising a first set of fields containing data related to the activity phases of the patient and a second set of fields containing data related to the rest phases of the patient,
    means for statistical processing receiving as input, said physiologic and physical signals and said status indicator, providing as output processed information, and selectively updating said plurality of fields based upon said processed information, wherein said means for statistical processing updates said first and second sets of fields using a respective inference rule of a plurality of inference rules, selectively as a function of the patient's status indicator, and
    means for analysis evaluating a plurality of clinical status indices based upon the data contained in the first and second sets of fields of the plurality of fields and evaluating a combined status index based the plurality of clinical status indices,
    wherein the each of the plurality of clinical status indices represents the patient's clinical status with one of a plurality of numerical values comprising a first signed value indicating improvement, a second signed value of the same value but opposite sign as the first signed value, the second signed value indicating degradation, and a null value indicating stability of the patient's clinical status relative to the patient's previous clinical status, and
    wherein the active medical device adjusts pacing parameters in response to the plurality of clinical status indices and the combined status index.

2. The device of claim 1, wherein:
    the first set of fields comprises a field representative of an elapsed duration in activity ($T_{act}$), a field representative of a level of the physiologic signal and a field representative of a level of the physical signal over said elapsed duration in activity, and
    the second set of fields comprises a field representative of an elapsed duration at rest ($T_{rep}$) and a field representative of the level of the physiologic signal over said elapsed duration at rest.

3. The device of claim 2, wherein the field representative of the level of the physical signal is a field containing an accumulation ($\Sigma Gi$) of successive digitized values of the physical signal over a predetermined duration, said accumulation being operated only when the status indicator indicates an activity phase of said activity phases.

4. The device of claim 2, wherein the field representative of the level of the physiologic signal over said elapsed duration in activity and the field representative of the level of the physical signal over said elapsed duration at rest, are fields that contain an average ($MV_{act}$; $MV_{rep}$) of successive digitized values of the physiologic signal over a predetermined duration, said average being updated only when the status indicator indicates respectively an activity phase of said activity phases or a rest phase of said rest phases of the patient.

5. The device of claim 1, wherein the analysis means further comprises means for comparing at least some of said data contained in the first and second sets of fields of the plurality of fields to a reference value.

6. The device of claim 1, wherein the means for analysis further comprise means for comparing variations of at least some of said data contained in the first and second sets of fields of the plurality of fields over a predetermined duration to a reference value.

7. The device of claim 5, wherein said reference value is calculated as a function of the average level taken by the corresponding datum over a predetermined duration.

8. The device of claim 7, wherein said reference value is bounded by high and/or low limits.

9. The device of claim 6, wherein said reference value is calculated as a function of the average level taken by the corresponding datum over a predetermined duration.

10. The device of claim 9, wherein said reference value is bounded by high and/or low limits.

11. The device of claim 1, wherein the means for analysis evaluates the combined status index based upon successive values taken by the at least one clinical status index of the plurality of clinical status indices.

12. The device of claim 11, wherein the device further comprises means for delivering a preventive alert, and wherein the means for delivering a preventive alert warns an overshoot of a threshold by the combined status index.

13. The device of claim 11, wherein said plurality of clinical status indices and the combined clinical status index are re-evaluated with a daily periodicity.

14. The device of claim 1, wherein the means for measuring a predominantly physiologic corporeal parameter further comprises a minute ventilation sensor.

15. The device of claim 1, wherein the means for measuring a predominantly physical corporeal parameter further comprises an acceleration sensor.

16. The device of claim 1, wherein the combined status index is derived by combining at least two of the plurality of clinical status indices to compensate the effect of the patient's improvement represented by a first clinical status index and the effect of the patient's degradation represented by a second clinical status index.

17. A non-transient computer readable storage medium storing executable program code comprising:

a first instruction set for generating a status indicator discriminating between activity phases and rest phases of a patient after receiving and evaluating data corresponding to a physiologic signal and a physical signal;

a second instruction set for statistical processing by receiving as input said physiologic and physical signals and said status indicator and providing output processed information;

a third instruction set for selectively updating memory fields based upon said output processed information as a function of the status indicator; wherein said memory fields comprise two sets of fields, a first set of fields containing data related the activity phases of the patient, a second set of fields containing data related to the rest phases of the patient; and a fourth instruction set for evaluating a plurality of clinical status indices based upon the data contained in the first and second sets of the memory fields; and a fifth instruction set for evaluating a combined status index based on the plurality of clinical status indices, wherein the each of the plurality of clinical status indices represents the patient's clinical status with one of a plurality of numerical values comprising a first signed value indicating improvement, a second signed value of the same value but opposite sign as the first signed value, the second signed value indicating degradation, and a null value indicating stability of the patient's clinical status relative to the patient's previous clinical status, and a sixth instruction set for causing an active medical device to adjust pacing parameters in response to the plurality of clinical status indices and the combined status index.

18. The non-transient computer readable storage medium of claim 17, wherein the combined status index is derived by combining at least two of the plurality of clinical status indices to compensate the effect of the patient's improvement represented by a first clinical status index and the effect of the patient's degradation represented by a second clinical status index.

* * * * *